(12) United States Patent
Rieuvernet (10) Patent No.: US 9,980,687 B2
(45) Date of Patent: May 29, 2018

(54) SEATING FOR A PORTABLE DIGITAL RADIOLOGICAL CASSETTE

(71) Applicant: TRIXELL, Moirans (FR)

(72) Inventor: Pierre Rieuvernet, Montbonnot Saint Martin (FR)

(73) Assignee: TRIXELL, Moirans (FR)

(*) Notice: Subject to any disclaimer, the term of this patent is extended or adjusted under 35 U.S.C. 154(b) by 0 days. days.

(21) Appl. No.: 14/653,799

(22) PCT Filed: Dec. 20, 2013

(86) PCT No.: PCT/EP2013/077858
§ 371 (c)(1),
(2) Date: Jun. 18, 2015

(87) PCT Pub. No.: WO2014/096430
PCT Pub. Date: Jun. 26, 2014

(65) Prior Publication Data
US 2015/0320373 A1 Nov. 12, 2015

(30) Foreign Application Priority Data
Dec. 21, 2012 (FR) .................................. 12 62665

(51) Int. Cl.
*G01T 1/17* (2006.01)
*G01T 1/20* (2006.01)
*A61B 6/00* (2006.01)

(52) U.S. Cl.
CPC .......... *A61B 6/4283* (2013.01); *A61B 6/4405* (2013.01); *A61B 6/4488* (2013.01)

(58) Field of Classification Search
CPC .... A61B 6/4283; A61B 6/4405; A61B 6/4488
See application file for complete search history.

(56) References Cited

U.S. PATENT DOCUMENTS

2005/0056922 A1* 3/2005 Vasoya .................. H01L 23/14
257/686
2007/0272873 A1* 11/2007 Jadrich ..................... G01T 1/20
250/370.11

(Continued)

FOREIGN PATENT DOCUMENTS

| CN | 1575423 A | 2/2005 |
|---|---|---|
| CN | 102327121 A | 1/2012 |

(Continued)

*Primary Examiner* — Eliza Osebaugh-Stewart
(74) *Attorney, Agent, or Firm* — Baker & Hostetler LLP (57) ABSTRACT

A portable radiological cassette is designed to equip a digital radiological system. The cassette comprises a digital ionizing radiation detector in the form of a flat panel which makes it possible to provide an image which depends on the radiation received, with an electronic board ensuring the control of the digital detector, and a casing ensuring the mechanical protection of the detector and the electronic board. The cassette additionally comprises a flat seating which supports the detector on a first one of its main faces, and supports the electronic board on a second one of its main faces, the two main faces being opposite. The seating is formed by a heterogeneous stack produced such that the surface thermal conductivity of the seating is greater than the transverse thermal conductivity of the seating.

16 Claims, 5 Drawing Sheets

(56) References Cited

U.S. PATENT DOCUMENTS

| | | | |
|---|---|---|---|
| 2011/0204239 A1* | 8/2011 | Yoshida | G01T 1/2985 250/361 R |
| 2011/0255666 A1 | 10/2011 | Liu et al. | |
| 2011/0316568 A1* | 12/2011 | Liu | A61B 6/4283 324/691 |
| 2012/0153172 A1 | 6/2012 | Sumi | |
| 2012/0168632 A1* | 7/2012 | Yagi | A61B 6/4233 250/366 |

FOREIGN PATENT DOCUMENTS

| | | |
|---|---|---|
| CN | 102579064 A | 7/2012 |
| FR | 2 605 166 A1 | 4/1988 |
| WO | 95/10411 A1 | 4/1995 |

* cited by examiner

SEATING FOR A PORTABLE DIGITAL RADIOLOGICAL CASSETTE

CROSS-REFERENCE TO RELATED APPLICATIONS

This application is a National Stage of International patent application PCT/EP2013/077858, filed on Dec. 20, 2013, which claims priority to foreign French patent application No. FR 1262665, filed on Dec. 21, 2012, the disclosures of which are incorporated by reference in their entirety.

FIELD OF THE INVENTION

The invention relates to a portable radiological cassette which is designed to equip a digital radiological system. The cassette comprises a digital ionizing radiation detector which makes it possible to provide an image which depends on the radiation received.

BACKGROUND

The radiological system additionally comprises a source of ionizing radiation, for example an x-ray tube, which makes it possible to generate radiation X, and a base station comprising a data processing system which makes it possible to synchronize the x-ray tube and the detector, and also makes it possible to carry out image processing, such as presenting the operator with the image which is corrected of all the faults which are inherent in the detector, and is improved for example by contour enhancement processing. An object, the image X of which is to be obtained, is placed between the source and the detector. A system of this type can be used in many applications, such as, for example, medical radiology and non-destructive testing. The invention can also be implemented for other types of radiation to be detected, notably gamma radiation.

In the past, the radiological systems were voluminous and difficult to move. It was necessary to position the object relative to the system in order to obtain the desired image. With the appearance of solid-state detectors, as described for example in French patent application FR 2 605 166, the detector became less voluminous, and it became possible to displace the detector relative to an object which remained fixed. For medical radiology, digital detectors were produced in the form of mobile cassettes, which it became possible to place in the immediate vicinity of a patient of whom an image was to be produced, when the state of health of the patient prevented him from being moved to a room reserved for radiology.

The mobile cassette essentially comprises a digital ionizing radiation detector in the form of a flat panel, and an electronic board, which notably ensures the control of the digital detector. The detector and the board are arranged in a casing which ensures their mechanical protection.

The cassette which is used in a portable system is subjected to far more handling than in a fixed radiological system, and its mechanical protection must be reinforced, notably in relation to impacts to which the cassette may be subjected during its displacements. More specifically, the digital detector is often made from photosensitive components which are arranged on a matrix on a glass plate which forms the most fragile element of the cassette. In addition to the impacts which could damage it, this plate is also sensitive to deformations, notably in the form of torsion.

The mechanical stresses which the cassette must withstand, and notably the digital detector, make it necessary to reinforce the structure of the casing, which is necessarily carried out to the detriment of the weight of the cassette.

In addition, the implementation of a radiological cassette involves particular stresses concerning thermal aspects. It has become apparent that the operation of the detector is adversely affected by the ambient temperature. It is possible to correct this adverse effect, for example by measuring the ambient temperature and correcting globally the image obtained from the detector. However, the presence of the electronic board in the casing of the cassette in the immediate vicinity of the detector may give rise to local effects in the radiological image. Firstly, the electronic board does not cover all of the surface of the detector. The area of the detector which faces the electronic board is therefore more affected thermally than the remainder of the detector. Secondly, locally in the electronic board, temperature differences may exist because of the presence of various components, the thermal dissipation of which can vary in large proportions. It then becomes difficult to correct the effects of these temperature differences.

SUMMARY OF THE INVENTION

The object of the invention is to improve the mechanical strength and thermal resistance of the existing cassettes, while limiting their increase in weight.

For this purpose, the invention relates to a portable radiological cassette comprising a digital ionizing radiation detector in the form of a flat panel, with an electronic board ensuring the control of the digital detector, and a casing ensuring the mechanical protection of the detector and the electronic board, characterized in that it additionally comprises a flat seating in a single piece which supports the detector on a first one of its main faces, and supports the electronic board on a second one of its main faces, the two main faces being opposite, and in that the seating is formed by a heterogeneous stack produced such that the surface thermal conductivity of the seating is greater than the transverse thermal conductivity of the seating, in that the seating comprises two outer skins which form the two main faces, and an inner material which is arranged between the two outer skins, the inner material and the two outer skins having a surface area which is substantially equal to that of the detector, and in that the thermal conductivity of the outer skins is greater than the thermal conductivity of the inner material.

"Surface thermal conductivity" means the thermal conductivity of the seating in directions which are supported by the two main faces of the seating, and "transverse thermal conductivity" means the thermal conductivity of the seating in a direction perpendicular to the directions which are supported by the two main faces of the seating.

BRIEF DESCRIPTION OF THE DRAWINGS

The invention will be better understood, and other advantages of it will become apparent from reading the detailed description of an embodiment provided by way of example, which description is illustrated by the accompanying drawing in which.

For the sake of clarity, the same elements will bear the same references in the different figures.

DETAILED DESCRIPTION

Figure 1:
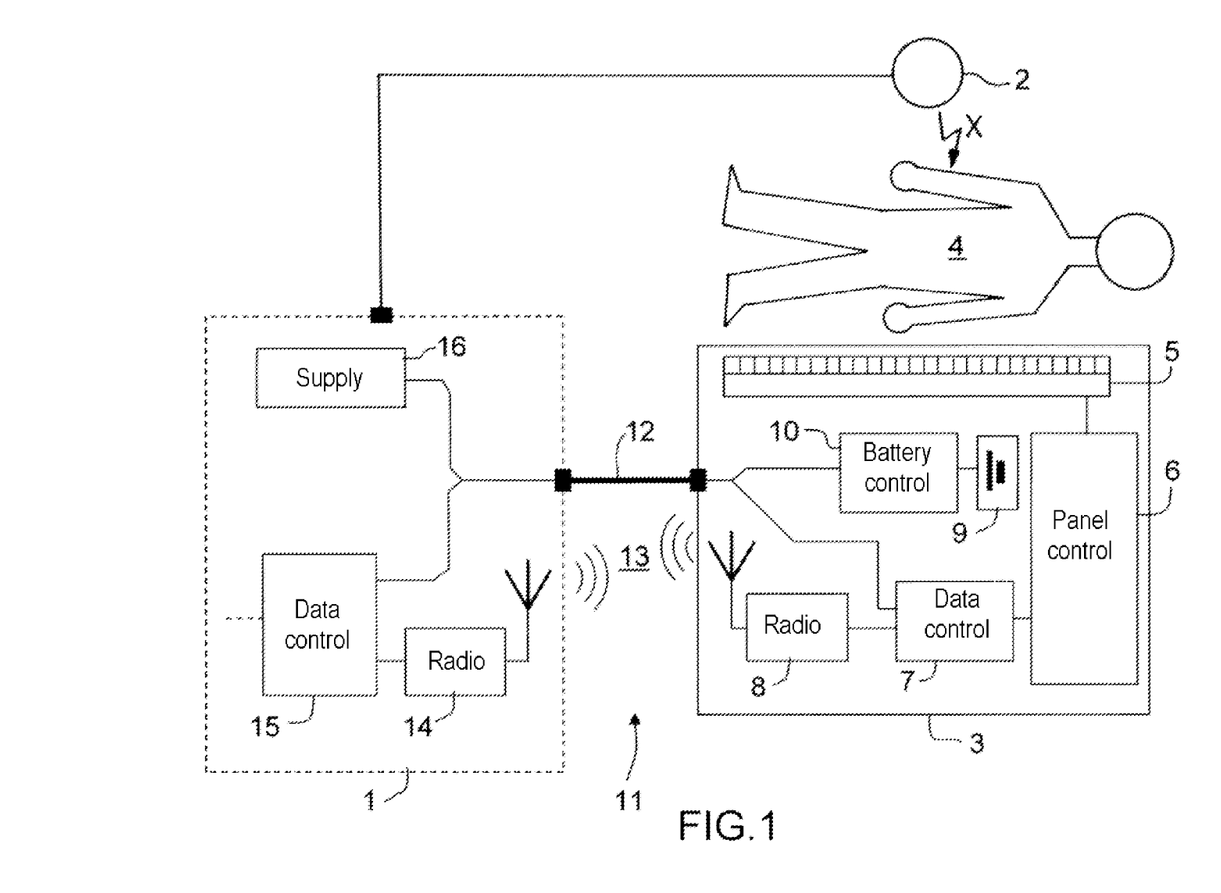
FIG. 1 represents an example of a radiological system which implements the invention.

FIG. 1 represents a radiological system which is designed for medical use. The system comprises a fixed base station 1, a radiation X generator 2, and a radiation detector in the form of a portable cassette 3. The cassette makes it possible to obtain an image of a patient 4 through whom there passes the radiation X obtained from the generator 2. The cassette 3 comprises a digital detector produced in the form of a flat panel 5 connected to a control module 6 which makes it possible to read the image obtained by the flat panel 5, and to digitize it by means of an analog—digital converter. The mobile cassette 3 also comprises a data control module 7, a radio module 8, a battery 9, and a battery control module 10.

The base station comprises a radio module 14, a data control module 15, and a supply 16.

Means 11 for communication between the cassette 3 and the base station 1 make it possible to transfer data such as the image between the cassette 3 and the base station 1. The data can circulate either from the base station 1 to the cassette 3, or from the cassette 3 to the base station 1. In the direction of the cassette 3, data for control of the flat panel 5 is involved for example, and in the direction of the base station 1, the data comprises for example images produced by the flat panel 5.

The means for communication can comprise a removable wired connection 12 and/or a wireless connection 13. The two connections 12 and 13 can both transfer data. The two radio modules 8 and 14 make it possible to exchange the data between the base station 1 and the cassette 3. The data control module 7 of the cassette 3 makes it possible to route the data received or originating from the control module 6 to one of the connections 12 or 13. Similarly, in the base station 1, the data control module 15 makes it possible to route the data received or originating from one of the connections 12 or 13. The supply 16 provides the electrical energy necessary for operation of the different modules of the base station 1 as well as the cassette 3.

The cassette 3 is supplied by means of the wired connection 12 or the battery 9. Advantageously, the system comprises means for recharging the battery 9. More specifically, the battery control module 10 measures the charge of the battery 9, and gives rise to its recharging if necessary.

Figure 2:
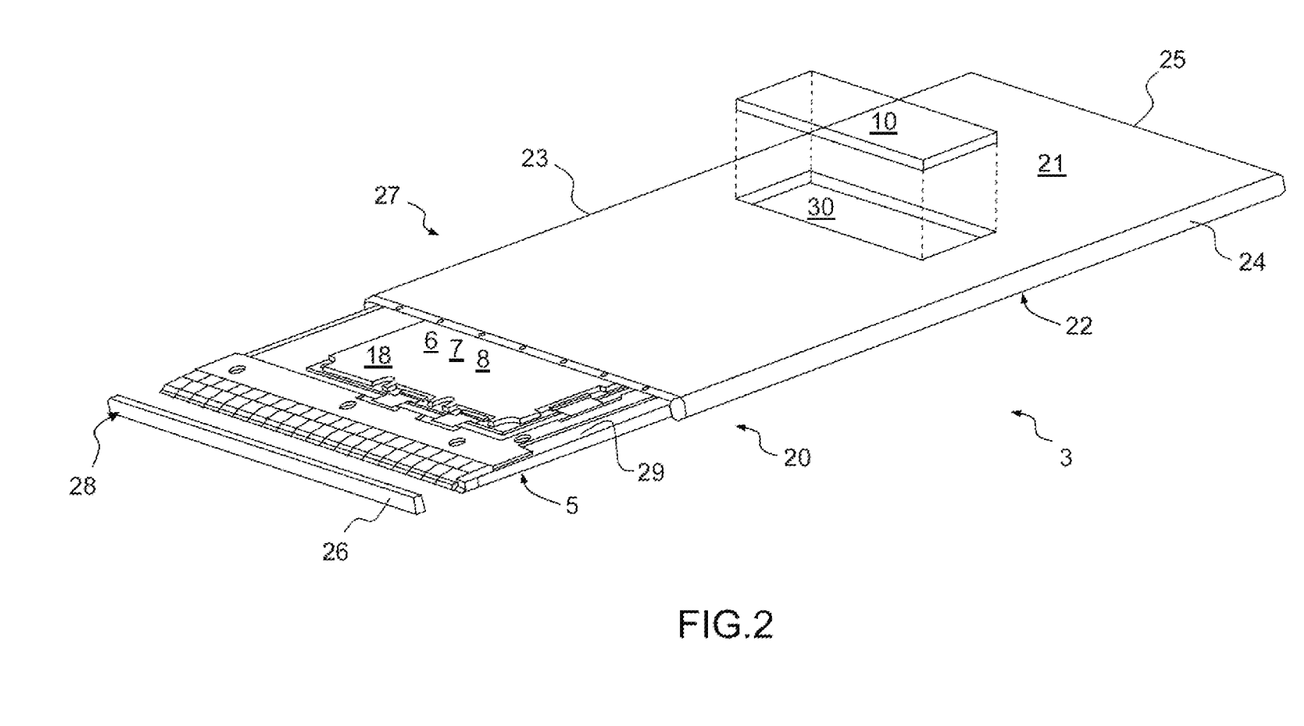
FIG. 2 represents an exploded view of a first variant of a portable cassette.

FIG. 2 represents a first variant of a portable cassette in an exploded view. In this case, the cassette bears the reference 17 and comprises a casing 20 with a substantially parallelepipedal form in which there are arranged the digital detector 5 and an electronic board 18 which ensures the control of the detector 5. With reference to FIG. 1, the electronic board 18 comprises for example the control module 6, the data control module 7, the radio module 8, and the battery control module 10. These four modules are provided only by way of example. They are not compulsory for implementation of the invention. The battery 9 is arranged on the exterior of the casing 20, in order to facilitate any replacement.

The casing 20 has six main faces 21 to 26, which delimit the parallelepipedal form. The six faces are parallel in pairs. The detector 5, in the form of a flat panel, has a radiation detection surface area which is close to that of the two largest faces 21 and 22. The parallel faces 25 and 26 are the two smallest faces of the casing 20.

The casing 20 comprises for example an envelope 27 made of a mechanical part in a single piece which forms the five faces 21 to 25 of the substantially parallelepipedal form, the two largest faces of which are 21 and 22. The casing 20 additionally comprises a stopper 28, which makes it possible to shut the face 26 of the substantially parallelepipedal form. Alternatively, the stopper 28 can shut the face 23 or the face 24. It is however advantageous to place the stopper 28 on one of the two smallest faces, in the example represented the face 26, in order to limit as far as possible the surface area of contact between the two elements 27 and 28 which form the casing 20, so as to facilitate the production of the sealing of the casing 20 and to increase the mechanical strength of the casing 20.

The fact of providing a part in a single piece on five faces makes it possible to strengthen the casing considerably. More particularly, the three smallest faces 23, 24 and 25 surround the casing 20 according to two perpendicular directions, which increases the strength of the casing 20 relative to torsion around axes which are parallel to the two largest faces 21 and 22.

The different elements which are arranged in the interior of the casing 20 are integral with one another and are slid into the envelope 27 via the face 26 in a movement of translation perpendicularly to this face. These different elements are for example fitted on a flat seating 29 with a surface area close to that of the two largest faces 21 and 22. The detector 5 is secured on the seating 29 on one side of the latter, and the electronic board 18 is secured on the seating 29 on the other side of the latter.

The battery 10 is accommodated in the interior of the parallelepipedal volume formed by the casing 20. The battery 10 is accommodated via the exterior of the cassette 17 in a recess 30 provided in the face 21. The face 22, opposite the face 21, is designed to have the ionizing radiation to be detected passing through it. The digital detector 5 is arranged in the interior of the casing 20 on the side of the face 22.

In the past, medical radiology used silver films which were handled in cassettes. Standard ISO 4090 defined the dimensions of the cassettes which envelop the silver films. The thickness of the cassettes, defined by the standard, is between 13 and 16 mm. Advantageously, the dimensions of the cassette 17 comply with the requirements of standard ISO 4090. More particularly, the overall thickness of the cassette 3 measured between the two largest faces 21 and 22 is smaller than 16 mm. This makes it possible to use the means for storage of silver cassettes for a digital cassette 17.

Figure 3:
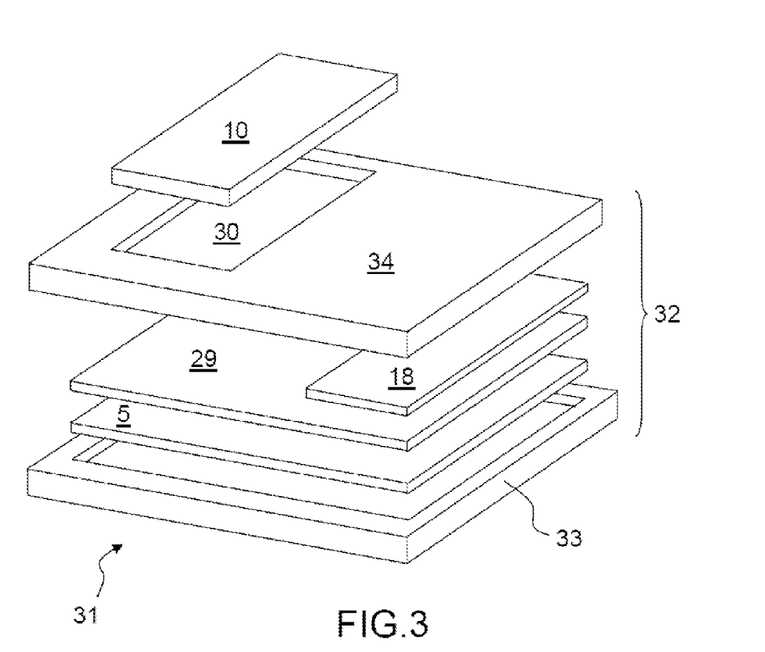
FIG. 3 represents an exploded view of a second variant of a portable cassette.

FIG. 3 represents in exploded view a second variant of a portable cassette, which in this case bears the reference 31. Assembled in the same manner, there are the seating 29, the detector 5 and the electronic board 18. There is also the battery 10. Unlike FIG. 2, the casing is different and in this case bears the reference 32. It is formed by two half shells 33 and 34, each of which forms one of the largest faces of the casing 31. The seating 29 and the different elements which are secured to it are arranged between the two half shells 33 and 34, which are then secured to one another, for example by screwing, at the periphery of the two large faces. As in the first variant, the battery 10 is accommodated in a recess 30 provided in the half shell 34.

The implementation of a part in a single piece in order to produce the envelope 27, as represented in FIG. 2, makes it possible to increase the mechanical strength. In fact, in the variant embodiment in FIG. 3, the presence of an assembly plane consisting of two distinct mechanical parts 33 and 34 at one of the large faces 21 or 22 reduces the strength relative to torsion and bending of the casing. In the variant in FIG. 3, the assembly plane is offset to one of the small faces of the casing, i.e. the face 26 in the example represented.

Figure 4:
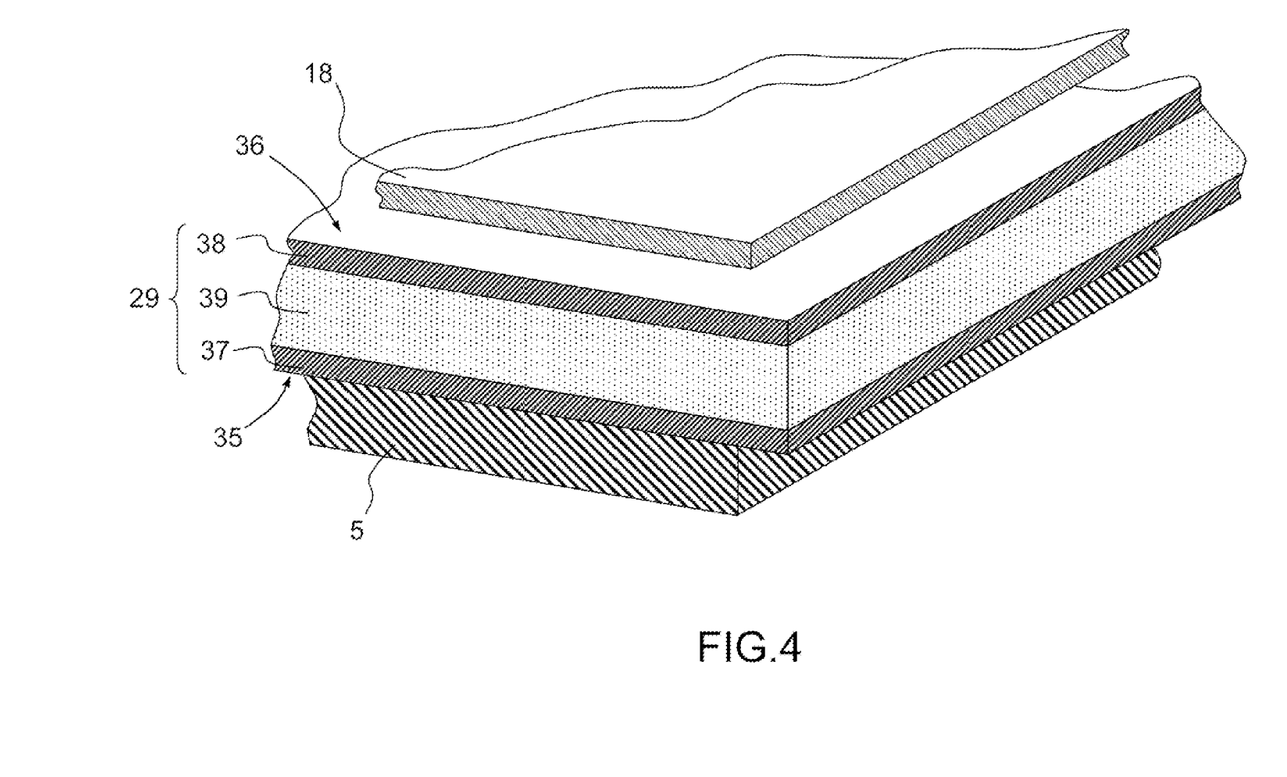
FIG. 4 represents in greater detail elements arranged in the interior of a casing of the cassette.

FIG. 4 represents in greater detail the elements arranged in the interior of the casing 20 or the casing 32, i.e. the seating 29 on which there are secured the detector 5 and the electronic board 18. The seating 29 is in the form of a globally flat plate, and comprises two main faces 35 and 36 opposite one another. The detector 5 is secured on the face 35, and the electronic board 18 is secured on the face 36. The assembly formed by the seating 29, the electronic board 18 and the detector 5 is self-supporting. It is possible to manipulate this assembly before it is assembled in one of the casings 20 or 32. In a parallelepipedal radiological cassette as represented in the two variants in FIGS. 2 and 3, it is attempted to make the best possible use of the surface area of the largest faces of the parallelepiped for the detection of the radiation X. The surface area of the detector 5 is virtually equal to that of the two large faces 21 and 22. The seating 29 ensures the function of a mechanical support for the detector 5 which occupies almost all of the surface area of the seating 29.

The seating is in a single piece, and constitutes an autonomous mechanical part. The seating 29 is formed by a stack comprising at least two outer skins 37 and 38 which form the two main faces of the seating 29, respectively 35 and 36, and an inner material 39, which is formed for example by an alveolar material arranged between the two skins 37 and 38. Because of its structure, an alveolar material has a high level of thermal resistance. As an alveolar material, it is possible to implement a foam, a light wood such as balsa, or a honeycomb structure. On the other hand, the skins 37 and 38 are advantageously made of a solid material. The density of the skins is advantageously greater than that of the inner material. The mechanical strength of the two outer skins 37 and 38 is advantageously greater than the mechanical strength of the foam 39. The foam 39 and the two skins 37 and 38 are globally flat, and have a surface area which is substantially equal to that of the detector 5.

It is possible to conceive of a seating made of stacks comprising a larger number of components, in order for example to form an alternation of layers of skin and foam.

When attempting to produce a cassette which complies with the dimensions imposed by the standard ISO 4090, the overall thickness of the cassette must not exceed 16 mm. In this thickness, there must be arranged the casing, the detector 5, the seating 29 and the electronic board 18 equipped with its components. During the design of the cassette, limitations are imposed by the active elements of the cassette, the detector 5 and the electronic board 18, which leaves little thickness available for the mechanical parts, and notably for the seating 29. Internal tests carried out by the applicant have shown that the thickness of the seating 29 must not exceed 2 mm. A thickness of up to 3 mm is acceptable, but this gives rise to greater constraints for the different elements included in the 16 mm stack. Hitherto, no stack which implements a foam sandwiched between two skins has been used for such small dimensions. In order to provide a mechanical support with a thickness of this type, the commonly accepted concept consists of providing a seating made of a homogenous material. Advantage is thus derived from the strength of the material selected, throughout its entire thickness.

However, the improvement of the mechanical strength of the seating is provided to the detriment of its resistance to the thermal constraints of a radiological cassette. More specifically, materials with good mechanical strength mostly have good thermal conductivity. The presence of the electronic board 18 opposite part of the detector 5 thus disrupts the operation of the detector 5 locally.

More specifically, production of the seating 29 from a homogenous metal material such as aluminum or titanium for example is recommended for good mechanical strength. On the other hand, these metals transmit heat particularly well, and generate effects which are difficult to correct. The thermal situation can be improved by making the seating 29 of a composite material, such as fibers embedded in resin for example. The narrow thickness of the seating 29 does not make it possible to improve the thermal situation completely.

The presence of the foam 39 in the stack of the seating 29 makes it possible to create rupture of a thermal bridge in a direction transverse to the seating. The skins 37 and 38 have thermal conductivity which is greater than the thermal conductivity of the foam 39. The electronic board 18 diffuses the heat emitted during its operation towards the skin 38 on which it is secured. As a result of the difference in surface and transverse thermal conductivity of the seating 29, the heat which is emitted by the electronic board 18 tends to be diffused more easily by conduction over the entire surface area of the skin 38, than transversely towards the other skin 37. This therefore provides a more homogenous temperature of the skin 37 in contact with the detector 5 than in the absence of rupture of a thermal bridge.

It will be appreciated that it is possible to produce other, heterogeneous stacks, in order to produce the seating 29, and notably stacks comprising more than three distinct layers.

With reference once more to the stack described, advantageously, the two skins 37 and 38 are produced from the same material, in order to simplify the production of the seating 29. The two skins 37 and 38 can be produced from a metal alloy, such as, for example, an alloy based on iron, copper or aluminum. Although certain iron alloys such as stainless steels with an austenitic structure have relatively low thermal conductivity of approximately 15 $W \cdot m^{-1} \cdot K^{-1}$, or even 10 $W \cdot m^{-1} \cdot K^{-1}$, it is possible to use these alloys for their mechanical strength property. It should be remembered that copper has thermal conductivity of 390 $W \cdot m^{-1} \cdot K^{-1}$, and that of aluminum is 237 $W \cdot m^{-1} \cdot K^{-1}$.

It is also possible to form the skins 37 and 38 from a composite material comprising fibers and resin in which the fibers are embedded. It is possible to implement numerous fibers such as, for example, glass fibers or carbon fibers. Carbon fibers have the advantage that they conduct electricity. They can thus fulfill a function of electromagnetic shielding between the electronic board 18 and the detector 5. In order to improve the mechanical strength, it is also possible to embed aramid fibers. It will be appreciated that it is possible to mix different types of fibers according to the result required.

In order to improve the homogeneity of the temperature of the skin 38, the skin can comprise fibers, the thermal conductivity of which is greater than 30 $W \cdot m^{-1} \cdot K^{-1}$. By way of example, carbon fibers exist based on pitch, known in the literature by the name of "pitch-based carbon fiber", the thermal conductivity of which exceeds 500 $W \cdot m^{-1} \cdot K^{-1}$. It will be appreciated that the skin 37 can comprise the same type of fibers.

In order to produce the skins 37 and 38, it is possible to use fibers organized in the form of fabrics or a mat, which can be dry, or pre-impregnated with resin.

More specifically, the carbon fibers can be arranged in the mold in the form of pre-impregnated fibers in a plurality of overlapping layers. It is also possible to arrange dry fibers in the mold, then inject the resin according to a technology known in the literature by the name of "resin transfer molding". This production method also makes it possible to improve the surface state of faces 35 and 36. The surface state makes it possible to facilitate putting into place of the electronic board 18 and the detector 5, notably by guaranteeing a constant thickness of the seating 29.

As an alternative to the fibers organized in the form of fabrics or a mat, it is also possible to use one-way fibers. In this case, in order to ensure good mechanical strength, the one-way fibers are arranged in a plurality of cross-layers. A particular arrangement of the one-way fibers has an advantage in terms of the thermal conductivity.

Figure 5:
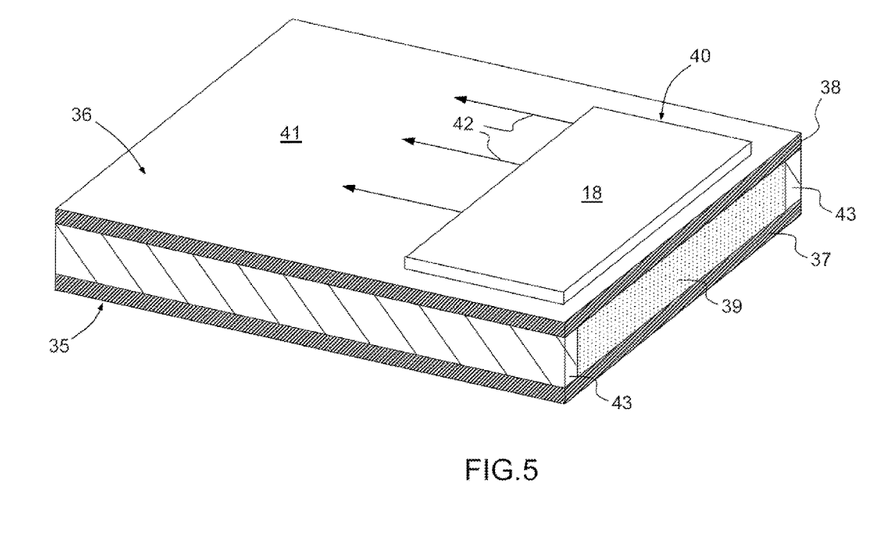
FIGS. 5 and 6 represent a variant of a seating forming the support of the elements arranged in the interior of the casing.

FIG. 5 makes it possible to indicate this advantage in greater detail. More specifically, it is common for the electronic board 18 to cover only a first part 40 of the seating 29. A second part 41 of the seating 29 is not covered by the electronic board 18. For the layer of one-way fibers which is arranged closest to the electronic board 18, it is advantageous to direct the fibers it contains from the first part 40 towards the second part 41. This direction is represented by arrows 42 in FIG. 5. This orientation of the fibers is produced such as to conduct heat generated by the electronic board 18 when it is operating, preferably from the part 40 to the part 41. This permits better homogeneity of the temperature of the skin 38 over its entire surface area, and more generally over the entire surface area of the seating 29.

In order to obtain a seating 2 mm thick, it is possible for example to use a foam 39 with a thickness of 1.2 mm and two skins made of composite materials based on carbon fibers 0.4 mm thick each. An example of foam which can be implemented is a poly methyl methacrylate foam known by its abbreviation PMMA. This type of foam has a thermal conductivity of approximately 0.04 $W \cdot m^{-1} \cdot K^{-1}$.

More generally, it is advantageous to select the materials of the skins and of the foam such that the ratio between the surface thermal conductivity of the seating and the transverse thermal conductivity of the seating is greater than 100.

In order to improve the mechanical strength of the seating 29, on the periphery of its main faces 35 and 36 it can comprise a mechanical reinforcement 43 which connects the skins 37 and 38. The reinforcement 43 is advantageously produced from the material implemented for the skins 37 and 38. The reinforcement 43 can follow all of the perimeter of the faces 35 and 36. Alternatively, the reinforcement 43 can follow only part of the perimeter of the faces 35 and 36, as represented in FIG. 5.

The reinforcement 43 can be used to improve the homogeneity of the temperature of the two skins 37 and 38. For this purpose, the reinforcement 43 advantageously has thermal conductivity which is greater than the transverse thermal conductivity of the seating 29 defined in the absence of the reinforcement 43. The reinforcement 43 thus produces a peripheral thermal bridge between the two faces of the seating 29. In fact, the main sources of heat of the cassette are electronic components which are situated on the electronic board 18. When these dissipater components are placed far from the periphery of the electronic board 18, the heat which they emit is dissipated on the skin 38 before reaching the reinforcement 43, the temperature of which is thus substantially homogenous. The thermal bridge produced by the reinforcement 43 thus makes it possible to preserve good homogeneity of the temperature of the skin 37 on which the digital detector 5 is secured.

When the skins 37 and 38 are made of composite materials, because of the presence of fibers arranged on the plane of the skin, their surface thermal conductivity is better than their transverse thermal conductivity. It is then difficult to produce the reinforcement 43 by means of a material of this type in order to fulfill the function of a thermal bridge between the two skins 37 and 38. For this purpose, it would be necessary to integrate transverse fibers in the reinforcement 43. Alternatively, in order to simplify the production of the reinforcement 43, it can be produced from a homogenous material such as, for example, an aluminum alloy, which provides the functions of both a mechanical reinforcement and a thermal bridge between the two skins 37 and 38.

Figure 6:
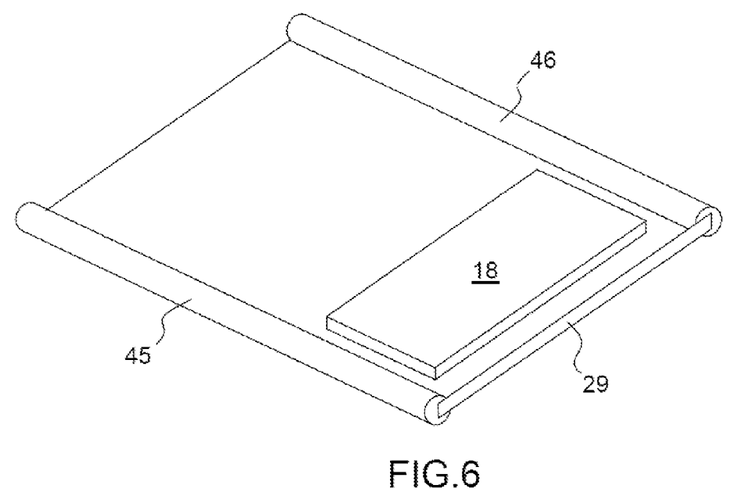

In the case of the first variant represented in FIG. 2, the seating 29, the detector 5 and the electronic board 18 are arranged in the envelope 27 via the face 26. More specifically, the assembly formed by these three assembled elements is slid into the envelope 27 via the face 26. The stopper 28 then shuts the face 26. Edges of the seating 29 ensure the guiding of the assembly during the insertion into the envelope 27. In order to facilitate this insertion, it is possible to add onto the seating 29 two profiles 45 and 46 which ensure the function of a slide, thus making it possible to facilitate the putting into position of the seating in the casing 20. These profiles are shown in FIG. 6. In order to limit the chain of dimensions between the envelope 27 and the seating 29, it is possible to secure the profiles 45 and 46 on the seating 29, for example by gluing, then machining the two profiles conjointly, such as to obtain good accuracy in the distance which separates the two profiles 45 and 46.

The invention claimed is:

1. A portable radiological cassette comprising a digital ionizing radiation detector in the form of a flat panel, with an electronic board ensuring the control of the digital detector, and a casing ensuring the mechanical protection of the detector and the electronic board, further comprising a flat seating in a single piece which supports the detector on a first one of its main faces, and supports the electronic board on a second one of its main faces, the two main faces being opposite, and the seating is formed by a heterogeneous stack produced such that the surface thermal conductivity of the seating is greater than the transverse thermal conductivity of the seating, and the seating comprises two outer skins which form the two main faces, and an inner material which is arranged between the two outer skins, the inner material and the two outer skins having a surface area which is substantially equal to that of the detector, and the thermal conductivity of the outer skins is greater than the thermal conductivity of the inner material; wherein, on the periphery of its main faces, the seating comprises a mechanical reinforcement which is located between the two outer skins and connects the skins, wherein the reinforcement forms a mechanical part with the two outer skins and the inner material such that the seating is in a single piece, and wherein the reinforcement has a thermal conductivity which is greater than the transverse thermal conductivity of the seating defined in the absence of the reinforcement.

2. The radiological cassette as claimed in claim 1, wherein a ratio between the surface thermal conductivity of the seating and the transverse thermal conductivity of the seating is greater than 100.

3. The radiological cassette as claimed in claim 1, wherein the casing has a substantially parallelepipedal form, the two largest faces of which are parallel to the detector, and in that the overall thickness of the cassette measured between the two largest faces is smaller than 16 mm.

4. The radiological cassette as claimed in claim 3, wherein the two outer skins are formed from a composite material comprising fibers and resin in which the fibers are embedded.

5. The radiological cassette as claimed in claim 4, wherein the skin which forms the second main face on which the electronic board is secured comprises fibers, the thermal conductivity of which is greater than 30 $W.m^{-1}.K^{-1}$.

6. The radiological cassette as claimed in claim 4, wherein the electronic board covers a first part of the seating and in that the skin which forms the second main face on which the electronic board is secured comprises a plurality of layers of one-way fibers, and in that, for the layer which is arranged closest to the electronic board, the one-way fibers are directed from the first part towards a second part of the seating which is not covered by the electronic board, such as to conduct heat which is generated by the electronic board during its operation, preferably from the first part to the second part of the seating.

7. The radiological cassette as claimed in claim 3, wherein the thermal conductivity of the skin which forms the second main face on which the electronic board is secured is greater than 10 $W.m^{-1}.K^{-1}$.

8. The radiological cassette as claimed in claim 1, wherein the inner material is formed by an alveolar material.

9. The radiological cassette as claimed in claim 1, wherein the casing has a substantially parallelepipedal form, the two largest faces of which are parallel to the detector, in that a first one of the two large faces is designed to have the ionizing radiation passing through it, in that the casing comprises an envelope produced in the form of a mechanical part in a single piece which forms five first faces of the substantially parallelepipedal form, the two largest faces and a stopper of which make it possible to shut a sixth face of the substantially parallelepipedal form, and in that an assembly formed by the seating, the detector and the electronic board is inserted into the envelope via the sixth face.

10. The radiological cassette as claimed in claim 9, wherein the seating comprises two added-on profiles which ensure the function of a slide during the insertion of the assembly formed by the seating, the detector and the electronic board into the envelope.

11. The radiological cassette as claimed in claim 1, wherein the mechanical strength of the two outer skins is greater than the mechanical strength of the inner material.

12. The radiological cassette as claimed in claim 1, wherein a thickness of the seating is less than 3 mm.

13. The radiological cassette as claimed in claim 1, wherein the reinforcement extends along a length of one side of the seating.

14. The radiological cassette as claimed in claim 1, wherein the reinforcement is sandwiched between the two outer skins of the seating.

15. The radiological cassette as claimed in claim 1, wherein the reinforcement is configured to follow the perimeter of the two faces.

16. The radiological cassette as claimed in claim 1, wherein the reinforcement is produced from the material implemented for the skins.

* * * * *